United States Patent [19]

Steinmetzer

[11] 4,384,136
[45] May 17, 1983

[54] PROCESS FOR RECOVERING AMINO ACIDS FROM PROTEIN HYDROLYSATES

[75] Inventor: Walter Steinmetzer, Süpplingen, Fed. Rep. of Germany

[73] Assignee: Societe d'Assistance Technique pour Produits Nestle S.A., Lausanne, Switzerland

[21] Appl. No.: 327,593

[22] Filed: Dec. 4, 1981

Related U.S. Application Data

[63] Continuation of Ser. No. 119,111, Feb. 6, 1980, abandoned.

[30] Foreign Application Priority Data

Feb. 16, 1979 [DE] Fed. Rep. of Germany ....... 2906034

[51] Int. Cl.³ .............................................. C07C 99/12
[52] U.S. Cl. .................................. 562/444; 562/445; 562/554
[58] Field of Search ................. 562/445, 444, 554, 516

[56] References Cited

U.S. PATENT DOCUMENTS

| | | | |
|---|---|---|---|
| 2,009,868 | 7/1935 | Barnett | 562/516 |
| 2,178,210 | 10/1939 | Mark | 562/516 |
| 2,443,391 | 6/1948 | Kirkpatrick | 562/554 |
| 2,471,053 | 5/1949 | Almquist et al. | 562/554 |
| 2,929,840 | 3/1960 | Vassel | 562/554 |
| 3,433,832 | 3/1969 | Swanson et al. | 562/554 |

FOREIGN PATENT DOCUMENTS

| | | | |
|---|---|---|---|
| 49-1515 | 1/1974 | Japan | 562/554 |
| 50-95221 | 7/1975 | Japan | 562/554 |

OTHER PUBLICATIONS

Tsuchiya, Chem. Abst., vol. 47, #3338e (1953).
Geipel, Chem. Abst., vol. 70 #29303g (1969).
Takayama et al., Chem. Abst., vol. 36, #44818 (1942).

*Primary Examiner*—James H. Reamer
*Attorney, Agent, or Firm*—Vogt & O'Donnell

[57] ABSTRACT

Amino acid fractions of different composition are obtained at different times by fractional filtration after neutralization of the hydrolysates. Tyrosine-rich and leucine-rich fractions are specifically treated and lead to the recovery of L-tyrosine, L-cystine, L-leucine and L-phenyl-alanine.

1 Claim, No Drawings

PROCESS FOR RECOVERING AMINO ACIDS FROM PROTEIN HYDROLYSATES

This is a continuation of application Ser. No. 119,111, filed Feb. 6, 1980, now abandoned.

This invention relates to a process for recovering amino acids from protein hydrolysates.

For recovering amino acids from vegetable or animal proteins, the proteins first have to be split up into their constituents, i.e. into the individual amino acids. In the known acid hydrolysis process, the proteins are subjected to prolonged heating with hydrochloric acid or sulphuric acid. Other known processes include hydrolysis of the proteins with alkalis and enzymatic hydrolysis.

Various specific precipitation methods have been proposed with a view to recovering amino acids from protein hydrolysates. Aromatic sulphonic acid, picric acid, mercury and copper salts are used for these precipitations. These processes are seriously complicated by the need to recover the precipitation reagents and by the use of organic solvents.

Separation of the amino acids by distillation of the ethyl esters is rarely used nowadays. Analytical separation of the amino acids can be carried out very effectively with ion exchangers. In the preparative recovery of amino acids, however, difficulties are caused by the large separation columns required, by the heavy dilution of the solution and by the contamination of the amino acid solutions by the buffer substances used for elution.

The present invention is the outcome of research to find a new separation process for recovering amino acids from protein hydrolysates which is simpler and which gives a greater yield at less cost, i.e. may be worked on an industrial scale.

The process according to the invention is characterised in that, after neutralisation of the hydrolysates, amino acid fractions of different composition are obtained at different times by fractional filtration.

It has been found that, during the neutralisation of a protein hydrolysate, the sparingly soluble amino acids crystallise out at different rates. The first fraction which precipitates immediately after neutralisation is enriched with leucine whilst the later fractions obtained after crystallisation times of at least 3 days are enriched with tyrosine and cystine. The separation of the sparingly soluble amino acids into at least two fractions is a feature of the present invention.

The starting material used for carrying out the process according to the invention may be obtained from a variety of protein sources rich in tyrosine, leucine, isoleucine and phenyl-alanine, such as for example desugared molasses, cereal or maizegerm, oil cake microorganisms, particularly yeasts, or casein. It is preferably obtained by the acid hydrolysis of protein sources such as these, optionally after the removal of ballast substances.

Preferred further stages of the separation process according to the invention are described in the following:

SEPARATION OF CYSTINE AND TYROSINE

The separation of cystine and tyrosine presents difficulties because, in their dipolar form, both these amino acids are very sparingly soluble in water. It has been found that, in changing from the dipolar to the anion form, the solubility of cystine increases more quickly than that of tyrosine in a certain pH-range. Thus, at a pH-value of 7.0, 0.04% of tyrosine and 0.02% of cystine are in solution, whereas at a pH-value of 9.2, 0.04% of tyrosine and 1.0% of cystine are in solution. By virtue of these changes in the solubility of the amino acids tyrosine and cystine, in a relatively narrow pH-range of 9.0 to 10.0, it is possible to separate these two amino acids.

Thus, one possible method of recovering L-tyrosine is characterised in that a fraction rich in tyrosine is dissolved at a pH-value of from 10 to 11, the resulting solution is filtered and the tyrosine is precipitated at a pH-value of from 8.5 to 10, preferably 9.5, separated off and purified by recrystallisation.

One possible method of recovering L-cystine is characterised in that the solution obtained after separation of the tyrosine is adjusted to a pH-value of from 3.0 to 6.0 and the cystine precipitated is separated off and purified by recrystallisation.

SEPARATION OF LEUCINE, ISOLEUCINE, METHIONINE AND TYROSINE

The two isomeric amino acids, leucine and isoleucine, have very similar physical properties and are therefore difficult to separate.

It has been found that, in changing from the dipolar to the cation form, the solubility of isoleucine increases more quickly than that of leucine in a certain pH-range. In a saturated sodium chloride solution, 0.4% of leucine and 0.5% of isoleucine are in solution at a pH-value of 6.0. At a pH-value of 1.5, 1.1% of leucine and 1.7% of isoleucine are in solution. By adjusting the solution to a specific isoleucine concentration, leucine can be precipitated at pH 1.0 to 2.0. Additional difficulties arise where methionine is present because these amino acids form co-precipitates with leucine. Accordingly, the methionine is converted into soluble methionine sulphoxide by oxidation, preferably before precipitation of the leucine.

Thus, one possible method of recovering L-leucine is characterised in that a fraction rich in leucine is dissolved in acid, the methionine is oxidised by the addition of oxidising agents and a crude leucine is precipitated at a pH-value of from 1.0 to 2.0, the isoleucine content of the solution preferably being adjusted to between 1.0 and 1.5%.

The exact pH-value in the range from 1.0 to 2.0 may be selected in dependence upon the tyrosine content of the leucine-rich fraction. The leucine may be further purified by repeating the precipitation process in the same pH-range.

EXTRACTION OF ISOLEUCINE, PHENYL-ALANINE, TYROSINE AND LEUCINE

The mother liquors from the precipitation of leucine contain the amino acids isoleucine, phenyl-alanine, tyrosine and residues of leucine. It has been found that the hydrochlorides of these amino acids may be extracted in very good yields from solutions containing sodiumchloride using a water-immiscible alcohol, particularly isobutanol or butanol. The extraction of amino acids and amino acid hydrochlorides from aqueous solutions being butanol or isobutanol is known. However, this extraction gives poor yields because the distribution coefficients of the amino acids or amino acid hydrochlorides in the butanol-water system are below 1.0. These distribution coefficients may be increased to a value above 10 by saturating the solution with sodium chloride.

Thus, one possible method of extracting leucine, isoleucine, phenyl-alanine and tyrosine is characterised in that a solution of the hydrochlorides of these amino acids saturated with sodium chloride is extracted with a water-immiscible alcohol, particularly isobutanol or butanol.

The valine and tyrosine content of the alcohol extract may be further reduced by washing the extract with water. This washing with water may be carried out directly at the head of the extraction column or in a separate apparatus. Following the addition of water, the alcohol may be azeotropically distilled of from the alcohol extract and returned to the extraction column. The hydrochloric acid may be removed from the aqueous solution of the amino acid hydrochlorides using a weakly basic anion exchanger and a mixture of leucine, isoleucine, phenyl-alanine and tyrosine may be obtained after concentration of the neutral solution.

RECOVERY OF PHENYL-ALANINE

Normally, phenyl-alanine is recovered together with tyrosine by adsorption on active carbon from acid solution. This process is attended by various disadvantages. Thus, the active carbon has to be activated by treatment with acetic acid, the quantity of phenyl-alanine adsorbed, based on the volume of active carbon, is very small and the phenyl-alanine has to be eluted with organic solvents, such as pyridine or aniline.

Accordingly, it is preferred in accordance with the invention to adsorb phenyl-alanine and tyrosine by treating a neutral salt-free amino acid solution with a strongly basic anion exchanger in hydroxide form, because it has been found that adsorption in this way enables five times the quantity of phenyl-alanine per unit volume to be taken up by comparison with adsorption on carbon.

Thus, one possible method of separating phenyl-alanine and tyrosine is characterised in that a neutral solution containing the hydrochlorides of these amino acids is passed over a weakly basic and over a strongly basic anion exchanger.

It has also been found that it is possible, simply by eluting the strongly basic anion exchanger with a hydrochloric acid solution, completely to remove the phenyl-alanine and the tyrosine from the ion exchanger. Where regeneration is carried out in the usual way using a 4% sodium hydroxide solution, the phenyl-alanine and tyrosine are only partly removed.

The eluates of the anion exchanger contain the hydrochlorides of the phenyl-alanine and tyrosine. Verification of the solubility behaviour in 6 n HCl showed that phenyl-alanine hydrochloride is sparingly soluble in the cold and highly soluble under heat. Tyrosine is more readily soluble in 6 n HCl in the cold. Thus, the eluate may be concentrated, its hydrochloric acid content adjusted to between 20 and 25%, sodium chloride separated off at 70° to 90° C. and the phenyl-alanine hydrochloride crystallised out by cooling. The phenyl-alanine hydrochloride may then be purified by recrystallisation and the hydrochloric acid removed by means of a weakly basic anion exchanger. Finally, pure L-phenyl-alanine may be obtained by concentrating the neutral solution by evaporation.

EXAMPLE 1

An acid protein hydrolysate is neutralised and the leucine-rich amino acid mixture which crystallises out is immediately filtered off. After a crystallisation time of at least 3 days, a second fraction of the sparingly soluble amino acids is separated off. This amino acid mixture is dissolved in dilute sodium hydroxide at pH 10.0 and the cystine concentration is adjusted to between 1.0 and 1.5% by the addition of water. After filtration of the solution, the tyrosine is precipitated at a pH-value of 9.5. After a crystallisation time of 24 hours, the crude tyrosine is filtered off, washed with water, dissolved in acid and precipitated under heat at pH 1.5 to 1.8. Under these precipitation conditions, a crystalline pure tyrosine is obtained.

The filtrate of the crude tyrosine is adjusted with acid to a pH-value of from 7.0 to 2.0 and preferably to a pH-value of 5.0 and, after 24 hours, the crude cystine which has crystallised out is separated off. This crude cystine is dissolved in acid and residues of tyrosine are adsorbed by the addition of active carbon. After filtration, the cystine is precipitated at a pH-value of 2.0 and separated off.

EXAMPLE 2

After neutralisation of a protein hydrolysate, the sparingly soluble amino acids precipitated are separated off as a first fraction rich in leucine. This amino acid mixture is dissolved at a pH-value of 0.5 and the isoleucine concentration is adjusted to approximately 1.5% by the addition of water. After the methionine content has been determined, the methionine is oxidised at 90° C. by the addition of an equimolar quantity of hydrogen peroxide. The solution is then filtered after the addition of active carbon, the pH-value is adjusted with dilute sodium hydroxide to between 1.0 and 1.5 and, after cooling, the crude leucine which has crystallised out is separated off. The crude leucine is re-dissolved at pH 0.5 and further purified by precipitation at pH 1.0 to 2.0. This process is repeated until the required purity of the L-leucine is reached.

The choice of the pH-value is determined by the tyrosine content of the solution. For tyrosine contents of the solution of 0.65; 0.8; 1.0; 1.2; 1.4; 1.6 and 1.8%, pH-values of 1.0; 1.65; 1.52; 1.42; 1.33; 1.26 and 1.16, respectively, are selected.

EXAMPLE 3

The filtrate from the precipitation of leucine is adjusted with hydrochloric acid to a pH-value of 0.5 and optionally saturated with sodium chloride. This solution is extracted in countercurrent with isobutanol in an extraction column. The ratio of isobutanol to the amino acid solution is adjusted to 1:1 or 1:2. In this process, the amino acids leucine, isoleucine and phenyl-alanine are extracted to a level of approximately 90%. The amino acids valine and tyrosine are extracted to a level of approximately 50%. The valine and tyrosine content is further reduced by washing the isobutanol extract with water. This washing with water is directly carried out at the head of the extraction column. after the addition of water, the isobutanol is azeotropically distilled off from the isobutanol extract and returned to the extraction column. The hydrochloric acid is removed from the aqueous solution of the amino acid hydrochlorides using a weakly basic anion exchanger and a mixture of leucine, isoleucine and phenyl-alanine is obtained after concentration of the neutral solution.

EXAMPLE 4

A mixture of the amino acid hydrochlorides of leucine, isoleucine, phenyl-alanine and tyrosine obtained by extraction with isobutanol is passed over a weakly basic anion exchanger in order to separate the hydrochloric acid. The neutral amino acid mixture is passed over a strongly basic anion exchanger in the hydroxide form. A pure solution of leucine and isoleucine is obtained in the liquid issuing from the column. Pure isoleucine may be obtained from this solution in known manner by extracting the copper complexes with methyl alcohol.

EXAMPLE 5

The anion exchanger column charged with phenyl-alanine and tyrosine is regenerated with one bed volume of 10% hydrochloric acid and then with one bed volume of 4% sodium hydroxide solution. The eluates from the hydrochloric acid regeneration are collected and concentrated. The acid concentration is adjusted to at least 20% by the addition of concentrated hydrochloric acid and the sodium chloride present is separated off at a temperature of from 70° to 90° C. After cooling of the solution, phenyl-alanine hydrochloride crystallises out and is purified by recrystallisation from 6 n HCl. To recover free phenyl-alanine, the phenyl-alanine hydrochloride is dissolved in water and the hydrochloric acid is removed by means of a weakly basic anion exchanger. Pure L-phenyl-alanine crystallises out on concentration of the neutral solution.

I claim:

1. A process for recovering amino acids from acid protein hydrolysates comprising the steps of:
    (a) neutralizing the protein hydrolysates to immediately crystallize a first fraction enriched with leucine which is thereafter separated by filtration;
    (b) continuing crystallization of the neutralized protein hydrolysates for at least 3 days to obtain a second fraction enriched with cystine and tyrosine which is thereafter separated by filtration;
    (c) dissolving the leucine-rich fraction in aqueous acid to form a solution;
    (d) adjusting the isoleucine content of the solution to between 1.0 and 1.5% by total weight by the addition or removal of water;
    (e) oxidizing the methionine contained in the solution by the addition of oxidizing agents;
    (f) adjusting the pH of the solution to a value in the range of from 1.0 to 2.0 depending upon the tyrosine content in the solution to precipitate crude leucine which is separated by filtration; and
    (g) purifying the separated leucine by repeatedly dissolving leucine in aqueous acid and precipitating the leucine at a pH range of from 1.0 to 2.0 until the desired degree of purity is obtained.

* * * * *

UNITED STATES PATENT AND TRADEMARK OFFICE
CERTIFICATE OF CORRECTION

PATENT NO. : 4,384,136
DATED : May 17, 1983
INVENTOR(S) : Walter Steinmetzer

It is certified that error appears in the above—identified patent and that said Letters Patent is hereby corrected as shown below:

Title Page, under the Sub-Heading "References Cited", "2,471,053 4/1949" should read --2,471,053 5/1945--.

Column 2, line 64, "being" should read --using--.

Column 3, line 14, "of" should read --off--.

Column 4, line 63, "after" should read --After--.

Signed and Sealed this

First Day of November 1983

[SEAL]

Attest:

Attesting Officer

GERALD J. MOSSINGHOFF

Commissioner of Patents and Trademarks